United States Patent
Zhebrovska et al.

(10) Patent No.: US 9,493,416 B2
(45) Date of Patent: Nov. 15, 2016

(54) N-METHYL-4-BENZYLCARBAMIDOPYRI-DINIUM CHLORIDE AND A PROCESS FOR ITS PREPARATION

(71) Applicant: Farmak International Holding GmbH, Vienna (AT)

(72) Inventors: Filya Zhebrovska, Kiev (UA); Grygorii Kostiuk, Kiev (UA); Mykhailo Vanat, Kiev (UA); Viktor Margitych, Kiev (UA)

(73) Assignee: Farmak International Holding GmbH, Vienna (AT)

( * ) Notice: Subject to any disclaimer, the term of this patent is extended or adjusted under 35 U.S.C. 154(b) by 0 days.

(21) Appl. No.: 14/368,505

(22) PCT Filed: May 16, 2013

(86) PCT No.: PCT/EP2013/060158
§ 371 (c)(1),
(2) Date: Jun. 24, 2014

(87) PCT Pub. No.: WO2013/171307
PCT Pub. Date: Nov. 21, 2013

(65) Prior Publication Data
US 2014/0357677 A1     Dec. 4, 2014

(30) Foreign Application Priority Data
May 18, 2012  (WO) ................. PCT/EP2012/059258

(51) Int. Cl.
*C07D 213/81*      (2006.01)
(52) U.S. Cl.
CPC .................................. *C07D 213/81* (2013.01)
(58) Field of Classification Search
CPC .................................................. C07D 213/81
See application file for complete search history.

(56) References Cited

FOREIGN PATENT DOCUMENTS

WO    WO 2011/157743 A1    12/2011

OTHER PUBLICATIONS

Zagorodnya "Action of isonicotinic acid derivatives on reproduction of Epstein-Barr virus" Mikrobiologichnii Zhurnal, 2011 73(2), 65-72 (abstract only).*
Golubeva "Estimation of amizon effect on experimental hepatitis induced by toxic doses isoniazide and rifampicin." Klinichna Farmatsiya, 2004 8(2), 60-62 (abstract only).*
Rozhnova "Investigation of the dynamics of release of nonsteroidal antiinflammatory drug Amizon from polymeric medicinal forms of prolonged action." Dopovidi Natsional'noi Akademii Nauk Ukraini 2007 (9), 125-130 (abstract only).*
Kondritzer "Investigation of Methyl Pyridinium-2-aldoxime Salts" Journal of Pharmaceutical Sciences vol. 50, No. 2, Feb. 1961, 109-112.*
ISR and Written Opinion of the ISA—PCT/EP2013/060158, Jun. 20, 2013, Zhebrovska et al.
Bukhtiarova et al. "Structure and antiinflammaotry activity of isonicontinic and nicotinic amides," Pharmaceutical Chemistry Journal, Springer NY LLC, US, vol. 31, No. 11, Jan. 1, 1997, pp. 597-599.
First Office Action issued in counterpart Chinese Patent Application No. 201380026081.6 together with English translation.

* cited by examiner

*Primary Examiner* — David K O Dell
(74) *Attorney, Agent, or Firm* — Mintz Levin Cohn Ferris Glovsky and Popeo, P.C.; Peter F. Corless (57) ABSTRACT

The present application relates to a new salt of N-methyl-4-benzylcarbami-dopyridine, a process for its preparation, a pharmaceutical composition comprising this compound and its use for the treatment or prevention of viral diseases.

16 Claims, 4 Drawing Sheets

N-METHYL-4-BENZYLCARBAMIDOPYRI-DINIUM CHLORIDE AND A PROCESS FOR ITS PREPARATION

RELATED APPLICATIONS

The present application is a national stage entry of International Application No. PCT/EP2013/060158, having an international filing date of May 16, 2013, which claims priority to International Application No. PCT/EP2012/059258, having an international filing date of May 18, 2012, the entire contents of which are incorporated herein by reference.

FIELD OF THE INVENTION

The present invention relates to a process for the preparation of N-methyl-4-benzylcarbamidopyridinium chloride, to the compound obtained by this process, to pharmaceutical compositions comprising this compound and their use in the treatment or prevention of viral diseases.

BACKGROUND OF THE INVENTION

N-methyl-4-benzylcarbamidopyridinium chloride (also referred to herein as "FAV00A-Cl") is a new salt form of the drug amizon which is N-methyl-4-benzylcarbamidopyridinium iodide (also referred to herein as "FAV00A-Io"). The pharmaceutically acceptable salts of carbabenzpyride have valuable pharmacologic properties.

Their principal property is the treatment and prevention of viral infections, more specifically those caused by influenza A viruses.

For the pharmaceutical use it is of major interest to have a highly pure substance. In addition, it is advisable to use a stable, robust and scalable industrial process resulting in a very consistent quality of the product which should be suitable for pharmaceutical formulations.

DESCRIPTION OF THE PRIOR ART

Amizon is described in, for example, SU 58612 (1975) which describes the synthesis of carbabenzpyride for pharmaceutical purposes, but there is no sufficient description in this reference how to obtain the drug in a reproducible manner.

Amizon is further described in Nesterova et al.: "Studying of Anti-Epstein-Barr Virus Activity of Amizon and their Derivative", ANTIVIRAL RESEARCH, EL-SEVIER B V, N L, Vol. 78, No. 2, 19 Mar. 2008, page A61, XP022541825 and Bukhtiarova T. A. et al.: "Structure and antiinflammatory activity of Isonicotinic and Nicotinic Amides", PHARMACEUTICAL CHEMISTRY JOURNAL, SPRINGER NEW YORK LLC, US, Vol. 31, No. 11, 1 Jan. 1997, pages 597-599.

Again, these references disclose amizon only in undefined form.

A new morphological form, i.e. the α-crystalline form of amizon, is described in applicant's co-pending patent applications WO 2011/158058 and WO 2011/157743. While this new morphological form shows a better dissolution profile when compared to the above-mentioned prior art form of amizon, its release profile still needs to be improved in an attempt to provide a rapidly dissolving formulation.

Thus, it is the technical problem underlying the present invention to provide a new salt of N-methyl-4-benzylcarbamidopyridine which has an improved release profile when compared to the above-mentioned prior art forms of N-methyl-4-benzylcarbamidopyridinium iodide.

SUMMARY OF THE INVENTION

The above object is achieved by providing a new salt, namely the chloride salt of N-methyl-4-benzylcarbamidopyridine by a process comprising the following step: quaterisation of the pyridinium ring atom of isonicotinic acid benzylamide with chloromethane according to the following reaction scheme

DETAILED DESCRIPTION OF THE INVENTION

As mentioned above, according to a first aspect, the present invention relates to a process for the preparation of N-methyl-4-benzylcarbamidopyridinium chloride comprising the following step: quaterisation of the pyridinium ring atom of isonicotinic acid benzylamide with chloromethane according to the following reaction scheme The reaction may be carried out in various organic solvents. Preferably polar solvents selected from 2-propanol, aqueous ethanol and acetonitrile are used.

In addition to the above-mentioned polar solvents acetone and alcohols other than ethanol may be mentioned.

According to a preferred embodiment of the present invention, aqueous ethanol comprising water in an amount of 1-20% is used as a polar solvent.

Reaction of the ingredients in ethanol 96% is the most suitable for industrial-scale FAV00A-Cl manufacture. Ethanol 96% is a cheaper solvent compared to 2-propanol and acetonitrile, and also less toxic. Besides, reaction in ethanol 96% is performed at lower pressure versus acetonitrile and using lower amounts of chloromethane (1.5 mol of chloromethane per 1 mol of isonicotinic acid benzylamide) compared to 2-propanol (2 mol of chloromethane per 1 mol of isonicotinic acid benzylamide). The FAV00A-Cl substance resulting from reaction in ethanol 96% is relatively pure for a technical grade product—admixtures are only up to 0.5%, and yield of the reaction is relatively high, i.e., about 80%.

In general, the reaction between isonicotinic acid benzylamide and chloromethane is carried out at a temperature in the range of 50-120° C., preferably at a temperature in the range of 80-100° C.

Usually, the reaction is carried out in an autoclave under pressure in the range of 0.1-1 MPa (1-10 bar), however, N-methyl-4-benzylcarbamidopyridinium chloride can also be prepared according to the present invention without pressure application. In this case, the reaction is carried out preferably in acetonitrile with heating and permanent passing of chloromethane gas through the reaction mixture without any pressure application, i.e. the reaction is carried out under normal or atmospheric pressure.

The reaction time is usually in the range of 1-20 h and preferably in the range of 12-16 h.

The molar ratio between isonicotinic acid benzylamide and chloromethane is usually in the range of 1-2, preferably 1-1.5, but depends on the solvent used. As mentioned above, low amounts of chloromethane (1.5 mol of chloromethane per 1 mol of isonicotinic acid benzylamide) can be used in case of ethanol 96% compared to the use of 2-propanol (2 mol of chloromethane per 1 mol of isonicotinic acid benzylamide).

N-methyl-4-benzylcarbamidopyridinium chloride produced by reaction with chloromethane can additionally be purified by recrystallisation, preferably from ethanol 96%. By doing so, a final product can be obtained that has an impurity level less than 0.5%. In particular, N-methyl-4-benzylcarbamidopyridinium chloride having less than or equal to 0.05% isonicotinic acid benzylamide can be obtained.

Depending on the level of impurities contained in N-methyl-4-benzylcarbamidopyridinium chloride, its melting temperature is in the range of 193° C. to 205° C.

The purest products obtained in the working examples shown hereinafter have a sharp melting point in the range of 198° C. to 203° C.

Finally, the present invention relates to a pharmaceutical composition comprising the new salt form, i.e. the chloride form, of N-methyl-4-benzylcarbamidopyridine.

These compositions may be in capsule form comprising the active ingredient in an amount of 0.01 to 100% by weight.

Such pharmaceutical compositions are useful in the treatment or prevention of viral diseases. Such viral diseases include influenza and influenza-like diseases caused by respiratory viral infection.

The present invention is further illustrated by the following examples and comparative examples.

Experimental Part

Example 1

260 ml of 2-propanol was cooled to 2-4° C. in a glass flask. 30.5 g (0.6 M) of chloromethane was dissolved at this temperature. 64 g (0.3 M) of isonicotinic acid benzylamide, 90 ml of cooled 2-propanol and 2-propanol solution saturated with chloromethane was loaded into an autoclave. The autoclave was closed and heated to 100° C. The mixture was incubated for 5 hours at this temperature. After that, the mixture was cooled by itself to the room temperature. The reaction mixture was transferred into a glass flask and cooled to 0-2° C. The sediment was filtered off and rinsed on the filter with 60 ml of cooled 2-propanol. The sediment was dried at room temperature for 24 hours. Output—74 g (the yield comprised 95% on isonicotinic acid benzylamide basis).

Analytical Parameters:

Assay—99.17%

Impurities—isonicotinic acid benzylamide—0.8%

Melting temperature—196.3-200.7° C.

Example 2

500 ml of ethanol 96% was cooled to 2-4° C. in a glass flask. 65 g (1.29 M) of chloromethane was dissolved at this temperature. 181.91 g (0.86 M) of isonicotinic acid benzylamide and ethanol 96% solution saturated with chloromethane was loaded into an autoclave. The autoclave was closed and heated to 100° C. The mixture was incubated for 5 hours at this temperature. After that, the mixture was cooled by itself to the room temperature. The reaction mixture was transferred into a glass flask and cooled to 0-2° C. The sediment was filtered off and rinsed on the filter with 50 ml of cooled ethanol 96%. The sediment was dried at room temperature for 24 hours. Output—182.2 g (the yield comprised 81% on isonicotinic acid benzylamide basis).
Analytical Parameters:
Assay—99.2%
Impurities—isonicotinic acid benzylamide—0.5%
Melting temperature—200.9-201.3° C.

Example 3

260 ml of acetonitrile was cooled to 2-4° C. in a glass flask. 43.91 g (0.87 M) of chloromethane was dissolved at this temperature. 122.89 g (0.58 M) of isonicotinic acid benzylamide, 300 ml of cooled acetonitrile and acetonitrile solution saturated with chloromethane was loaded into an autoclave. The autoclave was closed and heated to 100° C. The mixture was incubated for 3 hours at this temperature. After that, the mixture was cooled by itself to the room temperature. The reaction mixture was transferred into a glass flask and cooled to 0-2° C. The sediment was filtered off and rinsed on the filter with 100 ml of cooled acetonitrile. The sediment was dried at room temperature for 24 hours. Output—113 g (the yield comprised 75% on isonicotinic acid benzylamide basis).
Analytical Parameters:
Assay—100.7%
Impurities—isonicotinic acid benzylamide—0.07%
Melting temperature—187.4-201.4° C.

Example 4

210 ml of ethanol 96% was cooled to 2-4° C. in a glass flask. 28.86 g (0.57 M) of chloromethane was dissolved at this temperature. 80.78 g (0.28 M) of isonicotinic acid benzylamide and ethanol 96% solution saturated with chloromethane was loaded into an autoclave. The autoclave was closed and heated to 100° C. The mixture was incubated for 4 hours at this temperature. After that, the mixture was cooled by itself to the room temperature. The reaction mixture was transferred into a glass flask and cooled to 0-2° C. The sediment was filtered off and rinsed on the filter with 40 ml of cooled ethanol 96%. The sediment was dried at room temperature for 24 hours. Output—71.1 g (the yield comprised 72% on isonicotinic acid benzylamide basis).
Analytical Parameters:
Assay—97.74%
Impurities—isonicotinic acid benzylamide—0.5%
Melting temperature—201.4° C.

Example 5

260 ml of ethanol 96% was cooled to 2-4° C. in a glass flask. 37.45 g (0.74 M) of chloromethane was dissolved at this temperature. 104.8 g (0.49 M) of isonicotinic acid benzylamide and ethanol 96% solution saturated with chloromethane was loaded into an autoclave. The autoclave was closed and heated to 100° C. The mixture was incubated for 5 hours at this temperature. After that, the mixture was cooled by itself to the room temperature. The reaction mixture was transferred into a glass flask and cooled to 0-2° C. The sediment was filtered off and rinsed on the filter with 30 ml of cooled ethanol 96%. The sediment was dried at room temperature for 24 hours. Output—105.27 g (the yield comprised 82% on isonicotinic acid benzylamide basis).
Analytical Parameters:
Assay—99.2%
Impurities—isonicotinic acid benzylamide—0.5%
Melting temperature—201.1° C.

Example 6

540 ml of ethanol 96% was cooled to 2-4° C. in a glass flask. 70 g (1.37 M) of chloromethane was dissolved at this temperature. 196 g (0.92 M) of isonicotinic acid benzylamide and ethanol 96% solution saturated with chloromethane was loaded into an autoclave. The autoclave was closed and heated to 100° C. The mixture was incubated for 7 hours at this temperature. After that, the mixture was cooled by itself to the room temperature. The reaction mixture was transferred into a glass flask and cooled to 0-2° C. The sediment was filtered off and rinsed on the filter with 70 ml of cooled ethanol 96%. The sediment was dried at room temperature for 24 hours. Output—193.5 g (the yield comprised 79% on isonicotinic acid benzylamide basis).
Analytical Parameters:
Assay—91.1%
Impurities—isonicotinic acid benzylamide—0.5%
Melting temperature—201.3° C.

Example 7

30 g of technical grade FAV00A-Cl, 45 ml of ethanol 96% and 0.45 g of activated charcoal were loaded into a glass flask. The mixture was heated to boiling and incubated for 30 minutes. The charcoal was filtered off. The solution was cooled by itself to the room temperature. Subsequently, it was cooled to 0-2° C. and incubated for 3 hours at that temperature. The sediment was filtered off and rinsed on the filter with 10 ml of cooled ethanol 96%. The sediment was dried at room temperature for 24 hours. Output—26.12 g (the yield comprised 87% on technical grade FAV00A-Cl basis).
Analytical Parameters:
Assay—101.18%
Impurities—isonicotinic acid benzylamide—0.12%
Melting temperature—201.4° C.

Example 8

117.93 g of technical grade FAV00A-Cl, 205.5 ml of ethanol 96% and 2 g of activated charcoal were loaded into a glass flask. The mixture was heated to boiling and incubated for 30 minutes. The charcoal was filtered off. The solution was cooled by itself to the room temperature. Subsequently, it was cooled to 0-2° C. and incubated for 3 hours at that temperature. The sediment was filtered off and rinsed on the filter with 40 ml of cooled ethanol 96%. The sediment was dried at room temperature for 24 hours. Output—94.6 g (the yield comprised 80% on technical grade FAV00A-Cl basis).
Analytical Parameters:
Assay—99.21%
Impurities—isonicotinic acid benzylamide—0.2%
Melting temperature—199.6° C.

Example 9

547.5 g of technical grade FAV00A-Cl, 925 ml of ethanol 96% and 9.25 g of activated charcoal were loaded into a glass flask. The mixture was heated to boiling and incubated for 30 minutes. The charcoal was filtered off. The solution was cooled by itself to the room temperature. Subsequently, it was cooled to 0-2° C. and incubated for 3 hours at that temperature. The sediment was filtered off and rinsed on the filter with 150 ml of cooled ethanol 96%. The sediment was dried at room temperature for 24 hours. Output—433 g (the yield comprised 79% on technical grade FAV00A-Cl basis).
Analytical Parameters:
Assay—100.44%
Impurities—isonicotinic acid benzylamide—0.02%
Melting temperature—198.9° C.

We have also developed a method for FAV00A-Cl preparation without pressure application. The reaction is carried out in acetonitrile with heating and permanent passing of chloromethane gas through the reaction mixture.

Example 10

200 ml of acetonitrile and 42.26 g of isonicotinic acid benzylamide were loaded into a glass flask. The mixture was heated to 60° C. Chloromethane gas was permanently passed through the reaction mixture for 10 hours at this temperature. The solution was cooled by itself to the room temperature. Subsequently, it was cooled to 0-2° C. and incubated for 3 hours at that temperature. The sediment was filtered off and rinsed on the filter with 40 ml of cooled acetonitrile. The sediment was dried at room temperature for 24 hours. Output—18.1 g (the yield comprised 35% on isonicotinic acid benzylamide basis).
Analytical Parameters:
Assay—100.6%
Impurities—isonicotinic acid benzylamide—0.02%
Melting temperature—200-202.1° C.

Figure 1:
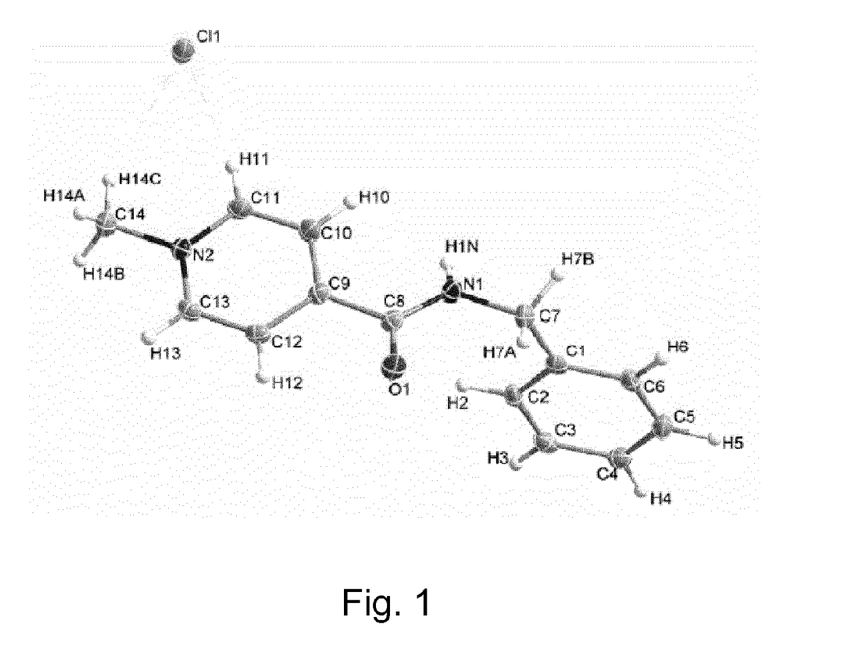
FIG. 1 shows a view of N-methyl-4-benzylcarbamidopyridinium chloride from the crystal structure showing the numbering scheme employed. Anisotropic atomic displacement ellipsoids for the non-hydrogen atoms are shown at the 50% probability level. Hydrogen atoms are displayed with an arbitrarily small radius.

Next, one sample of the N-methyl-4-benzylcarbamidopyridinium chloride prepared in the above-mentioned examples was taken (which is labelled in the following "Sample #2") to obtain the crystal structure information for this compound.

The final cell constants are shown below:
a=14.5489(5) Å, b=5.7837(2) Å, c=17.0030(6) Å, α=90°, β=114.935(2)°, γ=90°, volume=1297.38(8) Å$^3$. Final residuals: R1 [for 2481 I>2σ(I)]=3.10% wR2 [for all 2984 data]=8.28%.
Experimental Information for Sample#2

A white prism of $C_{14}H_{15}IN_2O$, approximate dimensions 0.10 mm×0.10 mm×0.10 mm, was used for the X-ray crystallographic analysis. The X-ray intensity data were measured at 100(2) K on a Bruker SMART APEX II system equipped with a graphite monochromator and a MoKα fine-focus sealed tube (λ=0.71073 Å) operated at 1250 W power (50 kV, 25 mA). The detector was placed at a distance of 40 mm from the crystal. 691 frames were collected with a scan width of 0.75° in ω. All frames were collected with an exposure time of 20 sec/frame. The total data collection time was 7 hours. The frames were integrated, scaled and merged with the Bruker SAINT software package using a narrow-frame integration algorithm. The integration of the data using a unconstrained (triclinic) cell yielded a total of 16473 reflections (24.19 data per frame at average) to a maximum θ angle of 30.509° (0.7 Å resolution), of which 8050 were independent. The final cell constants of a=5.78366(10) Å, b=14.54887(23) Å, c=17.00299(28) Å, α=114.9354(9)°, β=90.0462(10)°, γ=89.9763(10)°, cell volume=1297.36(4) Å$^3$, are based upon the refinement of the XYZ-centroids of 6226 reflections are selected on criteria I>20σ(I) in a range of 3.09°<θ<30.60°. Analysis of the data showed negligible decay during data collection. Data were corrected for absorption effects using the multiscan technique (SADABS). The calculated minimum and maximum transmission coefficients (based on crystal size) are 0.6022 and 0.7461. Symmetry constrained merge of dataset (monoclinic, space group #14 in International Tables for Crystallography, Volume A; $R_{sym}$=0.036, $R_{int}$=0.0377, $R_{sigma}$=0.0297) were performed with XPREP subroutine of Bruker SHELXTL package. Additional scaling, averaging and statistical treatment of reflections was carried out by Blessing algorithms were implemented in SORTAV code to reject systematic absence violations, inconsistent equivalents and beam-stop affected reflections by statistical evaluation of initial dataset. The structure was solved in the noncentro-symmetrical space group P2(1)/n, with Z=4 for the formula unit, $C_{14}H_{13}ClN_2O$ with SIR-92 software (all 18 non-hydrogen atoms were found in its correct positions, R=7.94%) refined using SHELXL-97 code, as implemented in the Bruker SHELXTL (Version 6.1.4) Software Package. The final anisotropic full-matrix least-squares refinement on $F^2$ with 172 (all hydrogen atoms, except those were at methyl groups, were refined) variables converged at R1=3.10%, for the observed data and wR2=8.27% for all data. Refinement of $F^2$ against ALL reflections. The weighted R-factor (denoted as wR) and goodness of fit (denoted as S) are based on $F^2$, conventional R-factors (denoted as R) are based on F, with F set to zero for negative $F^2$. The threshold expression of $F^2>2\sigma$ ($F^2$) is used only for calculating R-factors (gt) etc. and is not relevant to the choice of reflections for refinement. R-factors based on $F^2$ are statistically about twice as large as those based on F, and R-factors based on ALL data will be even larger. The goodness-of-fit was 1.043. The largest peak on the final difference electron density synthesis was 0.40 e$^-$/Å$^3$ and the largest hole was −0.49 e$^-$/Å$^3$ with an RMS deviation of 0.05 e/Å$^3$ observed in vicinity of Cl 1 atoms and could be considered as truncation error (bias) of Fourier difference synthesis. On the basis of the final model, the calculated density was 1.345 g/cm$^3$ and F(000)=552e$^-$.

All estimated standard deviations (here and after denoted as e.s.d's), except one in the dihedral angle between two l.s. planes) are estimated using the full covariance matrix. The cell e.s.d's are taken into account individually in the estimation of e.s.d's in distances, angles and torsion angles; correlations between e.s.d's in cell parameters are only used when they are defined by crystal symmetry. An approximate (isotropic) treatment of cell e.s.d's is used for estimating e.s.d's involving l.s. planes.

REFERENCES

Blessing, R. H. (1987). *Cryst. Rev.* 1, 3-58.
Blessing, R. H. (1989). *J. Appl. Cryst.* 22, 396-397.
Bruker (2007). APEX2, SAINT-Plus. Bruker AXS Inc., Madison, Wis., USA.
Bruker (2001). SADABS. Bruker AXS Inc., Madison, Wis., USA.
Altomare, A., Cascarano, G., Giacovazzo, C., Guagliardi, A., Burla, M. C., Poli-dori, G. & Camalli, M. (1994). J. Appl. Cryst. 27, 435.

TABLE 1

Crystal data and structure refinement for Sample#2.

| | |
|---|---|
| Identification code | Sample#2 |
| Empirical formula | $(C_6H_5)(CH_2)(NH)(CO)(C_5H_4N)(CH_3)^+Cl^-$ |
| Formula Weight | 260.72 |
| Temperature | 100(2) K |
| Diffractometer | Bruker SMART APEX II |
| Radiation source | fine-focus sealed tube, MoKα |
| Generator power | 1250 W (50 kV, 25 mA) |

TABLE 1-continued

Crystal data and structure refinement for Sample#2.

| | |
|---|---|
| Detector distance | 40 mm |
| Data collection method | ω scans |
| Theta range for data collection | 2.38 to 30.68° |
| Wavelength | 0.71073 Å |
| Variation during data collection | Negligible decay |
| Absorption correction | Semi-empirical from equivalents |
| Max. and min. transmission | 0.9 and 0.3449 |
| Crystal system | Monoclinic |
| Space group | P $2_1$/n |
| Unit cell dimensions | a = 14.5489(5) Å   α = 90° |
| | b = 5.7837(2) Å    β = 114.935(2)° |
| | c = 17.0030(6) Å   γ = 90° |
| Volume | 1297.38(8) Å$^3$ |
| Z | 4 |
| Density (calculated) | 1.345 g/cm$^3$ |
| Absorption coefficient | 0.28 mm$^{-1}$ |
| F(000) | 552 |
| Crystal size | 0.10 × 0.10 × 0.10 mm$^3$ |
| Theta range for data collection | 3.09 to 30.56° |
| Index ranges | −20 ≤ h ≤ 20, −8 ≤ k ≤ 8, −24 ≤ l ≤ 24 |
| Reflections collected | 16473 |
| Independent reflections | 2984 [R(int) = 0.037] |
| Completeness to theta = 27.5° | 99.9% |
| Refinement method | Full-matrix least-squares on F$^2$ |
| Structure solution technique | direct methods |
| Structure solution program | SIR-92 (Sheldrick, 2008) |
| Refinement technique | Full-matrix least-squares on F$^2$ |
| Refinement program | SHELXL-97 (Sheldrick, 2008) |
| Function minimized | $\Sigma w(F_o^2 - F_c^2)^2$ |
| Data/restraints/parameters | 2984/0/172 |
| Goodness-of-fit on F$^2$ | 1.043 |
| Final R indices [I > 2σ(I)] | R1 = 0.0310, wR2 = 0.0784 |
| R indices (all data) | R1 = 0.0405, wR2 = 0.0828 |
| Largest diff. peak and hole | 0.402 and −0.390 e · Å$^{-3}$ |

TABLE 2

Atomic coordinates (×10$^4$) and equivalent isotropic displacement parameters (Å$^2$ × 10$^3$) for Sample#2. U$_{eq}$ is defined as one third of the traces of the orthogonalized U$^{ij}$ tensor.

| | x | y | z | Ueq |
|---|---|---|---|---|
| Cl(1) | 9537 (1) | −2776 (1) | −1617 (1) | 24 (1) |
| C(1) | 8802 (1) | 7050 (2) | 2280 (1) | 15 (1) |
| C(3) | 8566 (1) | 4373 (2) | 3267 (1) | 19 (1) |
| C(7) | 8707 (1) | 7751 (2) | 1391 (1) | 18 (1) |
| C(2) | 8484 (1) | 4914 (2) | 2443 (1) | 17 (1) |
| C(4) | 8965 (1) | 5963 (2) | 3933 (1) | 20 (1) |
| C(6) | 9205 (1) | 8638 (2) | 2954 (1) | 17 (1) |
| C(5) | 9281 (1) | 8106 (3) | 3775 (1) | 21 (1) |
| N(1) | 8491 (1) | 5830 (2) | 794 (1) | 18 (1) |
| C(8) | 7555 (1) | 5401 (2) | 199 (1) | 16 (1) |
| C(9) | 7418 (1) | 3259 (2) | −344 (1) | 16 (1) |
| C(13) | 6253 (1) | 617 (2) | −1357 (1) | 17 (1) |
| C(11) | 7990 (1) | 189 (3) | −964 (1) | 21 (1) |
| C(12) | 6435 (1) | 2497 (2) | −822 (1) | 17 (1) |
| C(10) | 8206 (1) | 2058 (3) | −417 (1) | 21 (1) |
| O(1) | 6818 (1) | 6636 (2) | 65 (1) | 23 (1) |
| N(2) | 7028 (1) | −488 (2) | −1426 (1) | 16 (1) |
| C(14) | 6801 (1) | −2442 (2) | −2039 (1) | 20 (1) |

TABLE 3

Bond lengths [Å] and angles [°] for Sanple#2

| | |
|---|---|
| C(1)—C(2) | 1.3873 (19) |
| C(1)—C(6) | 1.3902 (18) |
| C(1)—C(7) | 1.5140 (18) |
| C(3)—C(4) | 1.381 (2) |
| C(3)—C(2) | 1.3914 (19) |
| C(3)—H(3) | 0.9500 |
| C(7)—N(1) | 1.4477 (17) |

TABLE 3-continued

Bond lengths [Å] and angles [°] for Sanple#2

| | |
|---|---|
| C(7)—H(7A) | 0.9900 |
| C(7)—H(7B) | 0.9900 |
| C(2)—H(2) | 0.9602 |
| C(4)—C(5) | 1.387 (2) |
| C(4)—H(4) | 0.9609 |
| C(6)—C(5) | 1.3881 (19) |
| C(6)—H(6) | 0.9755 |
| C(5)—H(5) | 0.9761 |
| N(1)—C(8) | 1.3343 (17) |
| N(1)—H(1N) | 0.8579 |
| C(8)—O(1) | 1.2269 (16) |
| C(8)—C(9) | 1.5068 (18) |
| C(9)—C(12) | 1.3855 (18) |
| C(9)—C(10) | 1.3907 (19) |
| C(13)—N(2) | 1.3423 (17) |
| C(13)—C(12) | 1.3706 (19) |
| C(13)—H(13) | 0.9244 |
| C(11)—N(2) | 1.3430 (17) |
| C(11)—C(10) | 1.374 (2) |
| C(11)—H(11) | 0.9356 |
| C(12)—H(12) | 0.9501 |
| C(10)—H(10) | 0.9465 |
| N(2)—C(14) | 1.4778 (17) |
| C(14)—H(14A) | 0.9800 |
| C(14)—H(14B) | 0.9800 |
| C(14)—H(14C) | 0.9800 |
| C(2)—C(1)—C(6) | 119.00 (12) |
| C(2)—C(1)—C(7) | 122.65 (12) |
| C(6)—C(1)—C(7) | 118.34 (12) |
| C(4)—C(3)—C(2) | 120.25 (13) |
| C(4)—C(3)—H(3) | 119.9 |
| C(2)—C(3)—H(3) | 119.9 |
| N(1)—C(7)—C(1) | 113.37 (11) |
| N(1)—C(7)—H(7A) | 108.9 |
| C(1)—C(7)—H(7A) | 108.9 |
| N(1)—C(7)—H(7B) | 108.9 |
| C(1)—C(7)—H(7B) | 108.9 |
| H(7A)—C(7)—H(7B) | 107.7 |
| C(1)—C(2)—C(3) | 120.43 (13) |
| C(1)—C(2)—H(2) | 119.8 |
| C(3)—C(2)—H(2) | 119.8 |
| C(3)—C(4)—C(5) | 119.71 (13) |
| C(3)—C(4)—H(4) | 120.1 |
| C(5)—C(4)—H(4) | 120.1 |
| C(5)—C(6)—C(1) | 120.60 (13) |
| C(5)—C(6)—H(6) | 119.7 |
| C(1)—C(6)—H(6) | 119.7 |
| C(4)—C(5)—C(6) | 120.01 (13) |
| C(4)—C(5)—H(5) | 120.0 |
| C(6)—C(5)—H(5) | 120.0 |
| C(8)—N(1)—C(7) | 121.64 (11) |
| C(8)—N(1)—H(1N) | 119.8 |
| C(7)—N(1)—H(1N) | 117.2 |
| O(1)—C(8)—N(1) | 124.45 (12) |
| O(1)—C(8)—C(9) | 119.06 (12) |
| N(1)—C(8)—C(9) | 116.48 (11) |
| C(12)—C(9)—C(10) | 118.34 (12) |
| C(12)—C(9)—C(8) | 117.23 (11) |
| C(10)—C(9)—C(8) | 124.38 (12) |
| N(2)—C(13)—C(12) | 120.07 (12) |
| N(2)—C(13)—H(13) | 120.0 |
| C(12)—C(13)—H(13) | 120.0 |
| N(2)—C(11)—C(10) | 120.63 (12) |
| N(2)—C(11)—H(11) | 119.7 |
| C(10)—C(11)—H(11) | 119.7 |
| C(13)—C(12)—C(9) | 120.31 (12) |
| C(13)—C(12)—H(12) | 119.8 |
| C(9)—C(12)—H(12) | 119.8 |
| C(11)—C(10)—C(9) | 119.46 (13) |
| C(11)—C(10)—H(10) | 120.3 |
| C(9)—C(10)—H(10) | 120.3 |
| C(13)—N(2)—C(11) | 121.16 (12) |
| C(13)—N(2)—C(14) | 118.68 (11) |
| C(11)—N(2)—C(14) | 120.14 (11) |
| N(2)—C(14)—H(14A) | 109.5 |
| N(2)—C(14)—H(14B) | 109.5 |
| H(14A)—C(14)—H(14B) | 109.5 |
| N(2)—C(14)—H(14C) | 109.5 |

TABLE 3-continued

Bond lengths [Å] and angles [°] for Sanple#2

| | |
|---|---|
| H(14A)—C(14)—H(14C) | 109.5 |
| H(14B)—C(14)—H(14C) | 109.5 |

TABLE 4

Anisotropic displacement parameters (Å$^2$ × 10$^3$) for Sample #2. The anisotropic displacement factor exponent takes the form: $-2\pi^2|\ h^2a^{*2}U^{11} + \ldots + 2hka^*b^*U^{12}$

| | U$^{11}$ | U$^{22}$ | U$^{33}$ | U$^{23}$ | U$^{13}$ | U$^{12}$ |
|---|---|---|---|---|---|---|
| Cl(1) | 15(1) | 28(1) | 25(1) | -9(1) | 5(1) | 3(1) |
| C(1) | 9(1) | 16(1) | 17(1) | -1(1) | 3(1) | 3(1) |
| C(3) | 14(1) | 17(1) | 26(1) | 1(1) | 9(1) | 0(1) |
| C(7) | 19(1) | 16(1) | 17(1) | -2(1) | 5(1) | -1(1) |
| C(2) | 13(1) | 16(1) | 20(1) | -4(1) | 4(1) | -1(1) |
| C(4) | 17(1) | 25(1) | 18(1) | 0(1) | 8(1) | 1(1) |
| C(6) | 14(1) | 16(1) | 20(1) | -2(1) | 5(1) | -1(1) |
| C(5) | 19(1) | 22(1) | 19(1) | -7(1) | 6(1) | -2(1) |
| N(1) | 15(1) | 20(1) | 16(1) | -3(1) | 3(1) | 3(1) |
| C(8) | 17(1) | 18(1) | 13(1) | 1(1) | 6(1) | 2(1) |
| C(9) | 16(1) | 19(1) | 11(1) | 2(1) | 4(1) | 2(1) |
| C(13) | 13(1) | 20(1) | 16(1) | 2(1) | 4(1) | 0(1) |
| C(11) | 14(1) | 26(1) | 20(1) | -4(1) | 6(1) | 4(1) |
| C(12) | 14(1) | 20(1) | 16(1) | 3(1) | 6(1) | 3(1) |
| C(10) | 12(1) | 29(1) | 19(1) | -6(1) | 4(1) | 1(1) |
| O(1) | 18(1) | 23(1) | 22(1) | -3(1) | 4(1) | 7(1) |
| N(2) | 16(1) | 16(1) | 13(1) | 1(1) | 5(1) | 1(1) |
| C(14) | 21(1) | 18(1) | 19(1) | -4(1) | 6(1) | 0(1) |

TABLE 5

Hydrogen coordinates (×10$^4$) and isotropic displacement parameters (Å$^2$ × 10$^3$) for Sample#2.

| | x | y | z | U$_{eq}$ |
|---|---|---|---|---|
| H(3) | 8347 | 2906 | 3373 | 22 |
| H(7A) | 8158 | 8909 | 1144 | 22 |
| H(7B) | 9347 | 8494 | 1453 | 22 |
| H(2) | 8206 (5) | 3800 (20) | 1984 (8) | 21 |
| H(4) | 9022 (1) | 5585 (7) | 4502 (10) | 24 |
| H(6) | 9438 (4) | 10140 (30) | 2848 (2) | 21 |
| H(5) | 9557 (5) | 9240 (20) | 4242 (8) | 25 |
| H(13) | 5596 (12) | 110 (10) | -1672 (6) | 20 |
| H(11) | 8519 (10) | -620 (15) | -1017 (1) | 25 |
| H(12) | 5885 (10) | 3282 (14) | -778 (1) | 20 |
| H(10) | 8887 (13) | 2524 (9) | -92 (6) | 25 |
| H(1N) | 8955 | 4802 | 907 | 24 |
| H(14A) | 6428 | -1875 | -2633 | 31 |
| H(14B) | 6390 | -3589 | -1908 | 31 |
| H(14C) | 7437 | -3158 | -1982 | 31 |

TABLE 6

Torsion angles [°] for Sample#2

| | |
|---|---|
| C(2)—C(1)—C(7)—N(1) | -14.13 (18) |
| C(6)—C(1)—C(7)—N(1) | 167.23 (11) |
| C(6)—C(1)—C(2)—C(3) | 0.18 (19) |
| C(7)—C(1)—C(2)—C(3) | -178.45 (12) |
| C(4)—C(3)—C(2)—C(1) | 0.0 (2) |
| C(2)—C(3)—C(4)—C(5) | 0.2 (2) |
| C(2)—C(1)—C(6)—C(5) | -0.61 (19) |
| C(7)—C(1)—C(6)—C(5) | 178.08 (12) |
| C(3)—C(4)—C(5)—C(6) | -0.6 (2) |
| C(1)—C(6)—C(5)—C(4) | 0.8 (2) |
| C(1)—C(7)—N(1)—C(8) | 99.85 (14) |
| C(7)—N(1)—C(8)—O(1) | 4.8 (2) |
| C(7)—N(1)—C(8)—C(9) | -176.01 (11) |
| O(1)—C(8)—C(9)—C(12) | -14.97 (18) |

TABLE 6-continued

Torsion angles [°] for Sample#2

| | |
|---|---|
| N(1)—C(8)—C(9)—C(12) | 165.83 (12) |
| O(1)—C(8)—C(9)—C(10) | 162.71 (13) |
| N(1)—C(8)—C(9)—C(10) | -16.49 (19) |
| N(2)—C(13)—C(12)—C(9) | -0.42 (19) |
| C(10)—C(9)—C(12)—C(13) | -0.57 (19) |
| C(8)—C(9)—C(12)—C(13) | 177.25 (11) |
| N(2)—C(11)—C(10)—C(9) | -0.2 (2) |
| C(12)—C(9)—C(10)—C(11) | 0.9 (2) |
| C(8)—C(9)—C(10)—C(11) | -176.77 (12) |
| C(12)—C(13)—N(2)—C(11) | 1.13 (19) |
| C(12)—C(13)—N(2)—C(14) | -177.23 (12) |
| C(10)—C(11)—N(2)—C(13) | -0.8 (2) |
| C(10)—C(11)—N(2)—C(14) | 177.53 (12) |

TABLE 7

Hydrogen bonds for Sample#2 [Å and °].

| D—H . . . A | d(D—H) | d(H . . . A) | d(D . . . A) | <(DHA) |
|---|---|---|---|---|
| N(1)—H(1N) . . . Cl(1)$^i$ | 0.86 | 2.33 | 3.1498 (12) | 161.0 |
| C(2)—H(2) . . . N(1) | 0.96 | 2.52 | 2.8576 (17) | 100.7 |
| C(7)—H(7A) . . . O(1) | 0.99 | 2.42 | 2.7981 (17) | 101.3 |
| C(11)—H(11) . . . Cl(1) | 0.94 | 2.46 | 3.3677 (14) | 162.6 |
| C(14)—H(14C) . . . Cl(1) | 0.98 | 2.86 | 3.7397 (14) | 150.1 |

Symmetry transformations used to generate equivalent atoms: (i) -x + 2, -y, -z

Results of comparative studies of active ingredient release profiles from a drug formulated as solid gelatine capsules using two salts of N-methyl-4-benzylcarbamidopyridine, namely the chloride and iodide salts labelled "FAV00A-Cl" and "FAV00A-Io" hereinafter.

In order to assess the FAV00A-Cl substance release rate from a finished medicinal product, studies of active ingredient release profiles were carried out for FAV00A-Cl 370.6 mg capsules, in 3 reference pharmacopeial buffer solutions with pH 1.2, 4.5, 6.8 and typical measurement conditions (1000 ml of 0.1M HCl; 100 rpm (basket); 1000 ml of acetate buffer solution pH 4.5; 100 rpm (basket); 1000 ml of phosphate buffer solution pH 6.8; 100 rpm (basket), respectively). Study results were compared against FAV00A-Io 500 mg capsules (with consideration of molecular weights of FAV00A-Cl and FAV00A-Io substances: the dosage of FAV00A-Cl substance 370.6 mg is equivalent to the dosage of FAV00A-Io substance 500 mg). The iodide salt FAV00A-Io used in the study was the α-crystalline form of amizon as described in applicant's co-pending patent applications WO 2011/158058 and WO 2011/157743.

Figure 2:
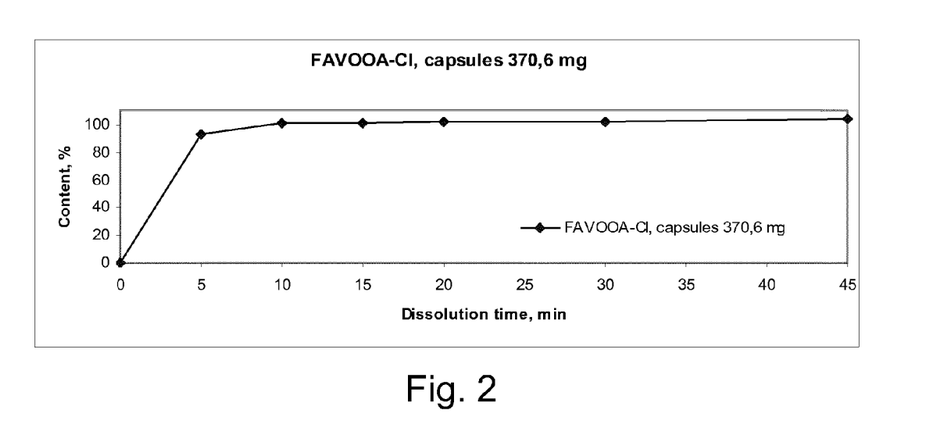
FIGS. 2, 4 and 6 show the release profile of N-methyl-4-benzylcarbamidopyridinium chloride contained in capsules in an amount of 370.6 mg.
Figure 3:
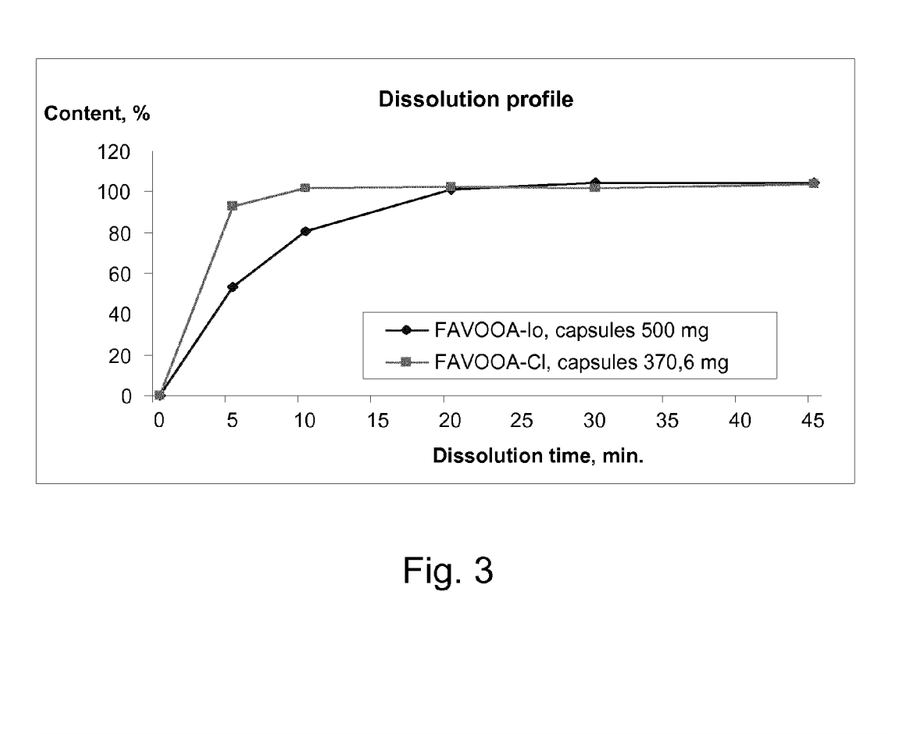
FIGS. 3, 5 and 7 show the dissolution profile of both the above-mentioned N-methyl-4-benzylcarbamidopyridinium chloride capsules and of capsules containing the corresponding iodide salt in an amount of 500 mg.
Figure 4:
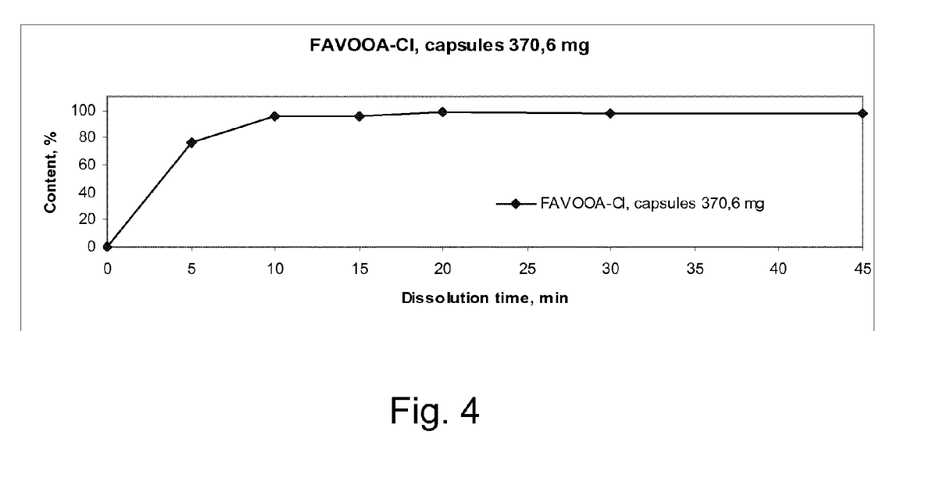
Figure 5:
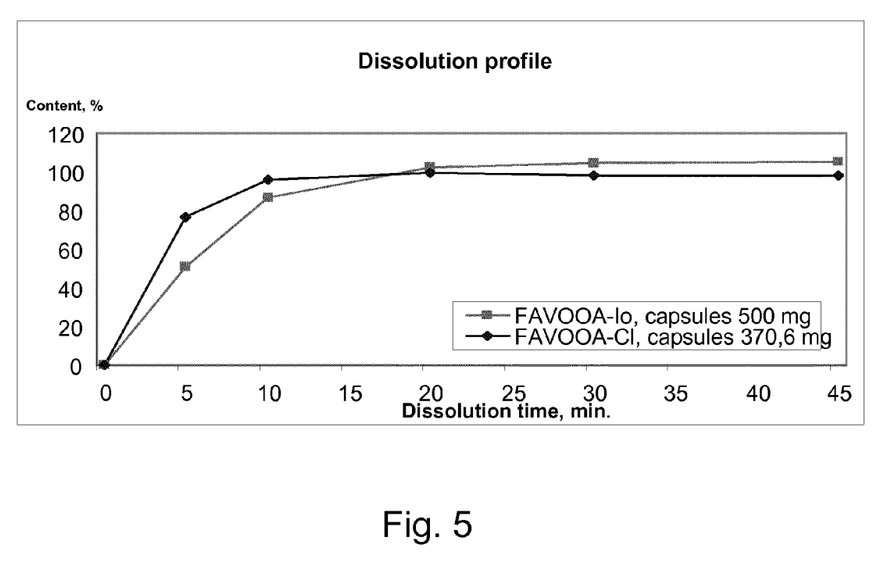
Figure 6:
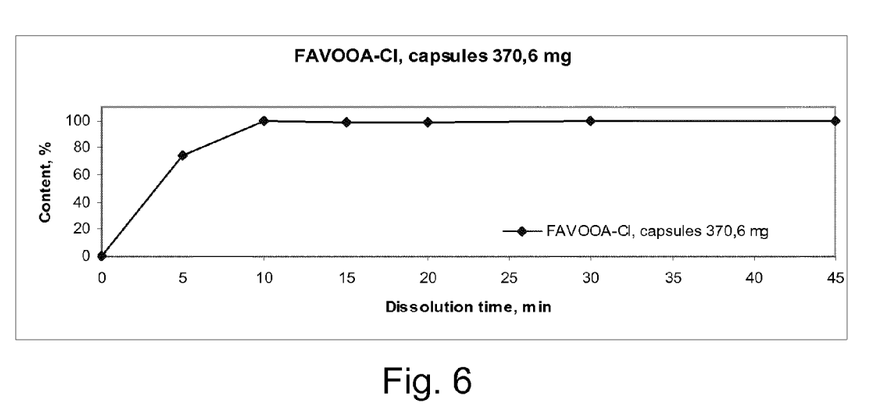
Figure 7:
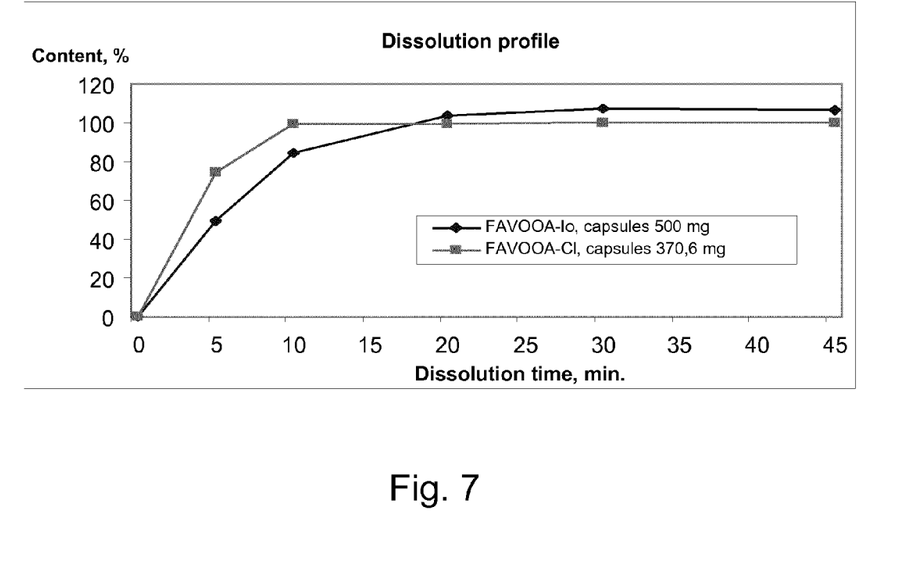

The results are depicted in FIGS. 2-7.

for 0.1M HCl:

On the 5-th minute, FAV00A-Cl is released faster than FAV00A-Io by 40%;

On the 10-th minute, FAV00A-Cl is released faster than FAV00A-Io by 20%;

for Buffer Solution with pH 4.5:

On the 5-th minute, FAV00A-Cl is released faster than FAV00A-Io by 25%;

On the 10-th minute, FAV00A-Cl is released faster than FAV00A-Io by 10% for Buffer Solution with pH 6.8:

On the 5-th minute, FAV00A-Cl is released faster than FAV00A-Io by 25%;

On the 10-th minute, FAV00A-Cl is released faster than FAV00A-Io by 15%

Dissolution profile of FAV00A-CI, 370.6 mg capsules
b. 10311
Conditions: 1000 ml of 0.1M HCl; 100 rpm (basket)

|  | 0 | 5 | 10 | 15 | 20 | 30 | 45 |
|---|---|---|---|---|---|---|---|
| Sample No. 1 | 0 | 97.51 | 106.16 | 103.81 | 105.11 | 106.06 | 107.32 |
| Sample No. 2 | 0 | 92.22 | 101.33 | 100.24 | 103.48 | 101.05 | 103.20 |
| Sample No. 3 | 0 | 94.34 | 102.12 | 102.62 | 104.21 | 104.07 | 105.61 |
| Sample No. 4 | 0 | 91.62 | 105.99 | 99.59 | 100.55 | 100.52 | 101.78 |
| Sample No. 5 | 0 | 93.73 | 100.36 | 99.61 | 100.94 | 99.84 | 104.48 |
| Sample No. 6 | 0 | 89.49 | 100.27 | 99.54 | 100.73 | 101.36 | 101.85 |
| Sample No. 7 | 0 | 83.24 | 99.37 | 99.22 | 101.31 | 100.92 | 101.66 |
| Sample No. 8 | 0 | 95.30 | 100.30 | 100.25 | 102.14 | 101.94 | 103.72 |
| Sample No. 9 | 0 | 93.10 | 100.84 | 101.31 | 102.66 | 100.96 | 103.17 |
| Sample No. 10 | 0 | 90.41 | 99.10 | 99.69 | 101.21 | 99.19 | 102.48 |
| Sample No. 11 | 0 | 99.41 | 100.67 | 100.73 | 103.62 | 102.50 | 104.94 |
| Sample No. 12 | 0 | 92.77 | 98.63 | 99.25 | 100.77 | 101.06 | 102.31 |
| Mean value | | | | | | | |
| FAV00A-CI, 370.6 mg capsules | 0 | 92.76 | 101.26 | 100.49 | 102.23 | 101.62 | 103.54 |
| SD | | | | | | | |
|  | 0 | 4.10 | 2.44 | 1.44 | 1.56 | 1.87 | 1.75 |

Dissolution profile of FAV00A-CI, 370.6 mg capsules
b. 10311
Conditions: 1000 ml of acetate buffer solution pH 4.5; 100 rpm (basket)

|  | 0 | 5 | 10 | 15 | 20 | 30 | 45 |
|---|---|---|---|---|---|---|---|
| Sample No. 1 | 0 | 74.79 | 95.31 | 95.56 | 97.55 | 97.28 | 98.34 |
| Sample No. 2 | 0 | 89.69 | 99.06 | 95.44 | 98.14 | 98.48 | 99.12 |
| Sample No. 3 | 0 | 77.05 | 95.95 | 95.95 | 97.82 | 99.59 | 97.97 |
| Sample No. 4 | 0 | 77.83 | 97.37 | 96.38 | 97.35 | 97.16 | 98.50 |
| Sample No. 5 | 0 | 70.11 | 96.62 | 95.72 | 97.96 | 96.98 | 98.37 |
| Sample No. 6 | 0 | 75.79 | 95.96 | 96.42 | 98.18 | 102.15 | 99.02 |
| Sample No. 7 | 0 | 84.60 | 94.74 | 95.97 | 100.81 | 97.52 | 97.35 |
| Sample No. 8 | 0 | 72.95 | 92.64 | 94.29 | 100.21 | 95.65 | 97.76 |
| Sample No. 9 | 0 | 74.25 | 91.54 | 95.66 | 101.14 | 96.53 | 96.74 |
| Sample No. 10 | 0 | 76.70 | 96.65 | 97.91 | 101.24 | 98.73 | 98.54 |
| Sample No. 11 | 0 | 69.48 | 94.95 | 95.70 | 99.11 | 96.43 | 97.19 |
| Sample No. 12 | 0 | 73.61 | 95.87 | 96.16 | 98.18 | 98.01 | 98.22 |
| Mean value | | | | | | | |
| FAV00A-CI, 370.6 mg capsules | 0 | 76.41 | 95.56 | 95.93 | 98.97 | 97.88 | 98.09 |
| SD | | | | | | | |
|  | 0 | 5.73 | 2.00 | 0.83 | 1.47 | 1.73 | 0.72 |

Dissolution profile of FAV00A-CI, 370.6 mg capsules
b. 10311
Conditions: 1000 ml of phosphate buffer solution pH 6.8; 100 rpm (basket)

|  | 0 | 5 | 10 | 15 | 20 | 30 | 45 |
|---|---|---|---|---|---|---|---|
| Sample No. 1 | 0 | 67.50 | 99.54 | 98.51 | 95.86 | 100.63 | 99.90 |
| Sample No. 2 | 0 | 73.56 | 99.95 | 98.04 | 97.76 | 98.45 | 97.87 |
| Sample No. 3 | 0 | 74.97 | 100.53 | 98.03 | 100.04 | 100.21 | 100.02 |
| Sample No. 4 | 0 | 75.43 | 99.78 | 101.63 | 100.56 | 102.88 | 102.89 |
| Sample No. 5 | 0 | 70.36 | 99.83 | 99.87 | 100.66 | 100.94 | 100.63 |
| Sample No. 6 | 0 | 72.75 | 97.33 | 95.31 | 97.76 | 100.23 | 99.51 |
| Sample No. 7 | 0 | 75.40 | 98.38 | 96.68 | 97.58 | 97.93 | 98.12 |
| Sample No. 8 | 0 | 79.32 | 97.49 | 99.17 | 97.73 | 99.74 | 98.39 |
| Sample No. 9 | 0 | 75.81 | 100.05 | 101.41 | 99.59 | 101.16 | 100.56 |
| Sample No. 10 | 0 | 86.71 | 100.24 | 100.18 | 100.24 | 100.46 | 100.59 |
| Sample No. 11 | 0 | 81.43 | 101.08 | 100.07 | 100.49 | 100.43 | 99.52 |
| Sample No. 12 | 0 | 60.70 | 98.00 | 98.90 | 99.18 | 99.67 | 100.01 |
| Mean value | | | | | | | |
| FAV00A-CI, 370.6 mg capsules | 0 | 74.49 | 99.35 | 98.98 | 98.95 | 100.23 | 99.83 |
| SD | | | | | | | |
|  | 0 | 6.64 | 1.24 | 1.84 | 1.57 | 1.27 | 1.36 |

Conclusion: Produced results of in vitro studies are indicative of faster release of FAV00A-Cl substance from finished medicinal product compared to FAV00A-substance in all 3 reference pharmacopoeial buffer solutions. Release of FAV00A-Cl substance from finished medicinal product in 15 min comprises more than 85%, which allows classifying this product as rapidly dissolving one. Faster release of the active ingredient from medicinal product also promotes the sooner onset of its therapeutic effect.

The invention claimed is:

1. N-methyl-4-benzylcarbamidopyridinium chloride having the formula

2. The N-methyl-4-benzylcarbamidopyridinium chloride according to claim 1 comprising impurities in the range of less than 0.5%.

3. The N-methyl-4-benzylcarbamidopyridinium chloride according to claim 2 wherein the content of isonicotinic acid benzylamide is less than or equal to 0.05%.

4. The N-methyl-4-benzylcarbamidopyridinium chloride according to claim 1 having a melting temperature in the range of 198 C to 203° C.

5. A pharmaceutical composition comprising the N-methyl-4-benzylcarbamidopyridinium chloride according to claim 1.

6. The pharmaceutical composition according to claim 5 which is in capsule form.

7. The pharmaceutical composition according to claim 6 wherein the capsule comprises the active ingredient in an amount of 0.01 to 100% by weight.

8. The N-methyl-4-benzylcarbamidopyridinium chloride according to claim 1 comprising impurities in the range of less than 0.5%, and wherein the content of isonicotinic acid benzylamide is less than or equal to 0.05%, and the N-methyl-4-benzylcarbamidopyridinium chloride according to claim 1 having a melting temperature in the range of 198 C to 203° C.

9. A pharmaceutical composition comprising the N-methyl-4-benzylcarbamidopyridinium chloride according to claim 2.

10. A pharmaceutical composition according to claim 8 which is in capsule form.

11. A pharmaceutical composition comprising the N-methyl-4-benzylcarbamidopyridinium chloride according to claim 3.

12. A pharmaceutical composition according to claim 11 which is in capsule form.

13. A pharmaceutical composition comprising the N-methyl-4-benzylcarbamidopyridinium chloride according to claim 4.

14. A pharmaceutical composition according to claim 13 which is in capsule form.

15. A pharmaceutical composition comprising the N-methyl-4-benzylcarbamidopyridinium chloride, wherein:
    impurities are present in an amount of less than 0.5%;
    the content of isonicotinic acid benzylamide is less than or equal to 0.05%; and
    the N-methyl-4-benzylcarbamidopyridinium chloride has a melting temperature in the range of 198 C to 203° C.

16. A pharmaceutical composition according to claim 15 which is in capsule form.

* * * * *